United States Patent [19]

Nitidandhaprabhas

[11] 4,017,628
[45] Apr. 12, 1977

[54] TREATMENT OF MANGE

[76] Inventor: Ovart Nitidandhaprabhas, 23/1 Tanpuying Pahol Lane, Ngam Vong Varn Road, Bangkhen, Bangkok, Thailand

[22] Filed: Dec. 22, 1975

[21] Appl. No.: 643,056

[30] Foreign Application Priority Data

Dec. 31, 1974 United Kingdom ............ 56173/74

[52] U.S. Cl. .......................... 424/263; 260/294.8 D
[51] Int. Cl.$^2$ ........................................ A61K 31/44
[58] Field of Search ............ 260/294.8 D; 424/263

[56] References Cited

OTHER PUBLICATIONS

Fenech, Chem. Abstracts, vol. 54, (22) 24, 723–b–e; Nov. 25, 1960.
Fenech et al., Chem. Abstracts, vol. 55, (16), 15, 465i–15, 466e Aug. 7, 1961.
Fenech, Chem. Abstracts, vol. 65, (3), 4439h–4440b Aug. 1, 1966.
Vigorita et al., Chem. Abstracts, vol. 76 (25) item 152, 784r June 19, 1972.
Dorland's Illustrated Medical Dictionary, 24th Ed. pp. –1615 Saunders Pub. 1965.

*Primary Examiner*—Alan L. Rotman
*Attorney, Agent, or Firm*—Pollock, Vande Sande & Priddy

[57] ABSTRACT

Compounds having the general formula:

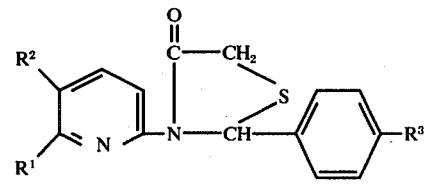

whrein $R^1$, $R^2$ and $R^3$ independently represent substituents selected from the group consisting of hydrogen, halogen, alkyl groups, alkoxy groups, aromatic groups, heterocyclic groups and any other functional groups.

The compounds may be prepared by the reaction of substantially equimolar portions of 2-aminopyridines with an aromatic aldehyde and thioglycollic acid.

The compounds are useful for treating skin diseases in animals such as mange in dogs.

9 Claims, No Drawings

TREATMENT OF MANGE

FIELD OF THE INVENTION

The invention relates to meta-thiazole derivatives or thiazolidones and to their preparation. The invention also relates to veterinary compositions containing such compounds useful for treating skin diseases in animals.

BACKGROUND OF THE INVENTION

I have found that the novel meta-thiazole derivatives can be synthesised in a similar manner to the preparation of α-alkyl-quinoline-γ-carboxylic acids disclosed by O. Doebner in Annalen der Chemie 242, 265 (1887). In the Doebner reaction an aldehyde, pyruvic acid and aniline are reacted together and a heterocyclic ring is formed fused to the benzene ring giving rise to the quinoline derivative. The compounds of the present invention may be synthesised by the reaction of 2-aminopyridines with an aromatic aldehyde and thioglycolic acid in which the heterocyclic thiazole ring is formed attached to pyridine nucleus by the amino nitrogen atom.

BRIEF SUMMARY OF THE INVENTION

According to the present invention there is provided compounds having the general formula:

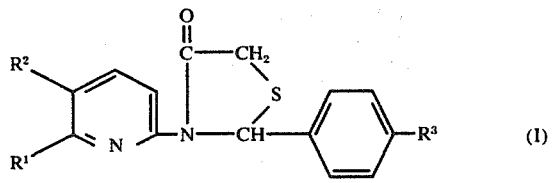

(I)

in which $R^1$, $R^2$ and $R^3$ may be the same or different and each represent a hydrogen atom, halogen atom, alkyl group, alkoxy group, aromatic group or heterocyclic group, or any other functional group. Preferred alkyl and alkoxy groups are those having from 1 to 6 carbon atoms and the preferred aromatic group is a benzene ring.

The compounds of Formula I may be prepared by the reaction shown in the following equation:

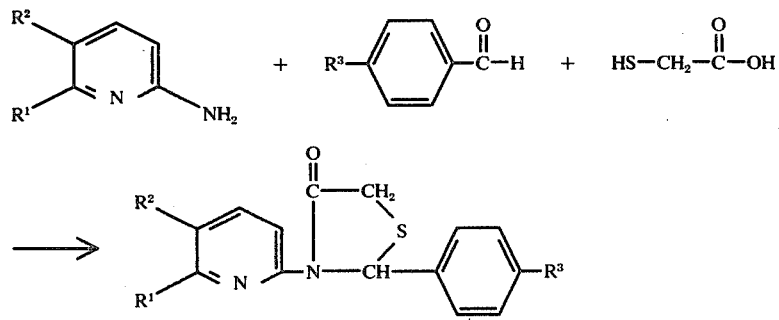

in which $R^1$, $R^2$ and $R^3$ are as defined previously.

The general method of preparation of the compounds of the invention is to reflux substantially equimolar portions of each reactant in a solvent, e.g. ethanol, for several hours. The resultant mixture may then be left to stand at room temperature until about half the solvent has evaporated and is then poured into excess water. The resulting solution is made alkaline with concentration $NH_4OH$ and the oily product that settles is separated and dissolved in a solvent e.g. ethanol. Crystallization of the product may take several days.

I have found that the compounds of Formula I are effective against skin diseases and in particular are effective against mange in dogs.

Therefore also according to the invention there is provided a veterinary composition comprising a compound of Formula I and a physiologically acceptable carrier.

Such compositions may be in the form of a solution or dispersion or an ointment. The compositions have the advantage that as well as being effective against skin diseases they may be licked by the animal to which they are applied without harmful effect since the compounds of Formula I are not toxic in view of their very low solubility in water.

EXAMPLES OF THE INVENTION

The invention will now be illustrated by the following Examples.

EXAMPLE 1

Preparation of

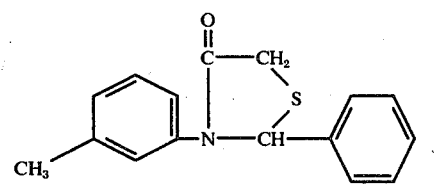

0.05 mole of each of 6-methyl-2-aminopyridine, benzaldehyde and thioglycolic acid were added to 100ml of ethanol and refluxed for 3 hours. The mixture was left to stand at room temperature to evaporate half the solvent and poured into excess water. The resulting solution was made alkaline with concentrated $NH_4OH$ and the oily product dissolved in ethanol and crystallized out of solution. The melting point of the product was 116° to 117° C.

The resultant product was assigned the above structure on the basis of i.r. and mass spectral date. The compound shows a molecular ion at $m/e = 270$ whose fragmentation is consistent with the above structure. The carbonyl stretching vibration at 1670 $cm^{-1}$ is appropriate for a tertiary amide.

EXAMPLES 2 to 4

Examples 2 to 4 were prepared as in Example 1. The products and melting points are summarised in the following Table:

| EXAMPLE | R¹ | R² | R³ | MELTING POINTS |
|---------|----|----|----|----------------|
| 2 | H | H | H | 105–107° C |
| 3 | H | H | OCH₃ | 116–117° C yield about 20% |
| 4 | H | Cl | H | 118–119° C |

EXAMPLE 5

An aqueous saturated solution of the product of Example 3 was prepared by heating 100mg of the compound in 1 liter of distilled water for 3 minutes to ensure saturation was obtained.

100 skin diseased dogs in Thailand were treated by applying the saturated solution to the infected areas on a two-to-four time daily basis. Complete recovery of hair was brought about in the three weeks or more, depending on the extent of the disease. The success of the treatment was more than 90%. The saturated solution was active against both sarcoptic and demodectic manges as confirmed by qualified veterinarians.

What is claimed is:

1. A method of treating mange in mammals which comprises applying to the infected area a composition comprising:
   a. a compound having the formula:

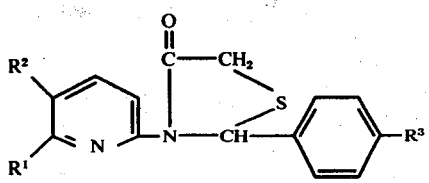

wherein $R^1$, $R^2$, and $R^3$ independently represent substituents selected from the group consisting of hydrogen, halogen, alkyl groups containing 1 to 6 carbon atoms, alkoxy groups containing 1 to 6 carbon atoms, and phenyl; and
   b. a physiologically acceptable carrier.
2. The method of claim 1 wherein said mammal is a dog.
3. The method of claim 1 wherein said mange includes sarcoptic mange.
4. The method of claim 1 wherein said mange includes demodectic mange.
5. The method of claim 1 wherein $R^1$, $R^2$, and $R^3$ are each hydrogen.
6. The method of claim 1 wherein $R^1$ is $CH_3$ and $R^2$ and $R^3$ are each hydrogen.
7. The method of claim 1 wherein $R^1$ and $R^3$ are each hydrogen and $R^2$ is chlorine.
8. The method of claim 1 wherein $R^1$ and $R^2$ are each hydrogen and $R^3$ is $OCH_3$.
9. The method of claim 1 wherein said physiologically acceptable carrier is water.

* * * * *